United States Patent [19]

Hasson et al.

[11] Patent Number: 5,176,687
[45] Date of Patent: Jan. 5, 1993

[54] DISPOSABLE POUCH CONTAINER FOR ISOLATION AND RETRIEVAL OF TISSUES REMOVED AT LAPAROSCOPY

[76] Inventors: Harrith M. Hasson, 2043 N. Sedgwick, Chicago, Ill. 60614; Herbert F. D'Alo, 37 Forest Hills Dr., Madison, Conn. 06443

[21] Appl. No.: 698,567

[22] Filed: May 10, 1991

[51] Int. Cl.⁵ ............................................. A61B 17/22
[52] U.S. Cl. ................................... 606/114; 606/127
[58] Field of Search ............... 606/113, 114, 127, 128; 604/52, 53

[56] References Cited

U.S. PATENT DOCUMENTS

| | | | |
|---|---|---|---|
| 30,471 | 10/1860 | Dudley | 606/127 |
| 798,839 | 9/1905 | Stowe | 606/113 |
| 3,472,230 | 10/1969 | Fogarty | 606/127 |
| 4,271,839 | 6/1981 | Fogarty | 606/127 X |
| 4,324,262 | 4/1982 | Hall | 606/127 X |
| 4,657,020 | 4/1987 | Lifton | 606/127 |
| 4,997,435 | 3/1991 | Demeter | 606/127 |

FOREIGN PATENT DOCUMENTS

| | | | |
|---|---|---|---|
| 2604024 | 5/1976 | Fed. Rep. of Germany | 606/127 |
| 2927726 | 1/1981 | Fed. Rep. of Germany | 606/127 |
| 2170715 | 8/1986 | United Kingdom | 606/127 |

*Primary Examiner*—Peter A. Aschenbrenner
*Attorney, Agent, or Firm*—Wood, Phillips, VanSanten, Hoffman & Ertel

[57] ABSTRACT

An apparatus for facilitating the safe removal of a mass from within a body cavity. The apparatus has a membrane that can be selectively placed in a) an expanded state wherein the membrane defines an internal space for reception of a mass to be removed from the cavity and b) a collapsed state wherein the membrane occupies less space than it does in its expanded state. The membrane has an entryway that is in communication with the internal space defined by the membrane with the membrane in its expanded state. Structure is provided for closing the membrane entryway from a location remote drom the entryway.

28 Claims, 6 Drawing Sheets

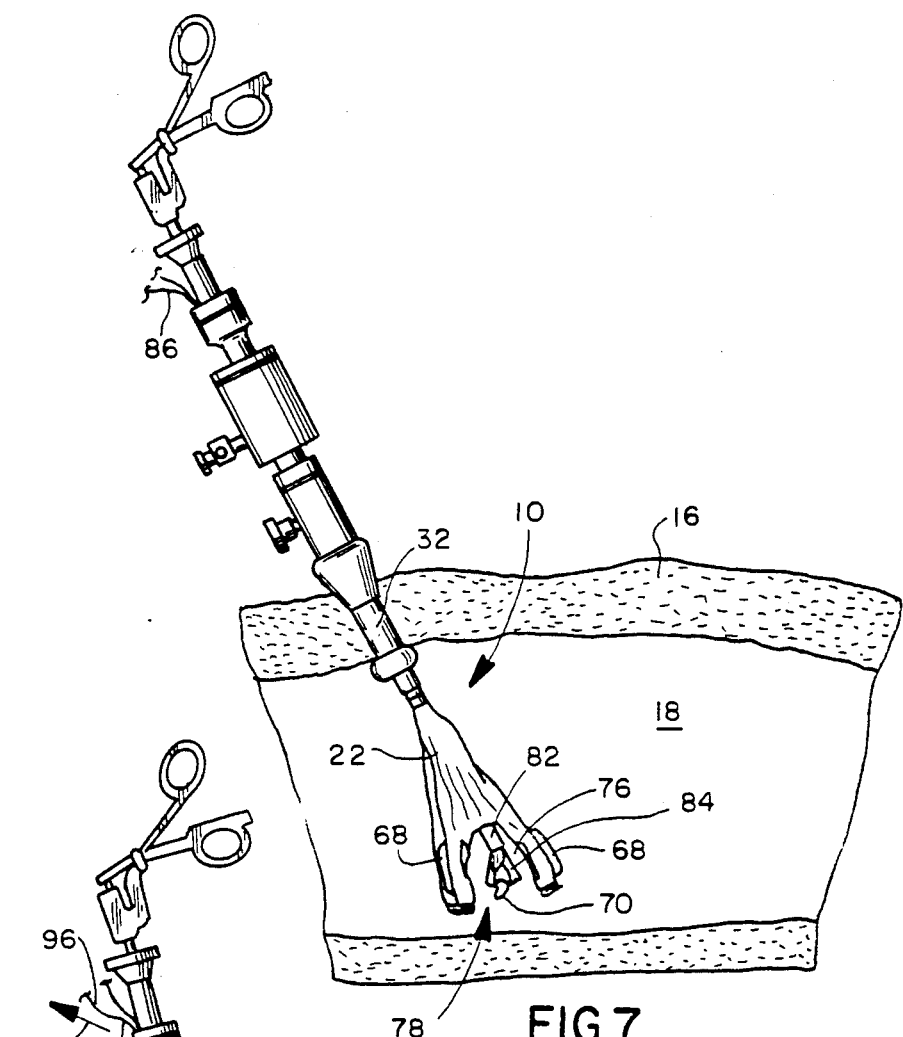
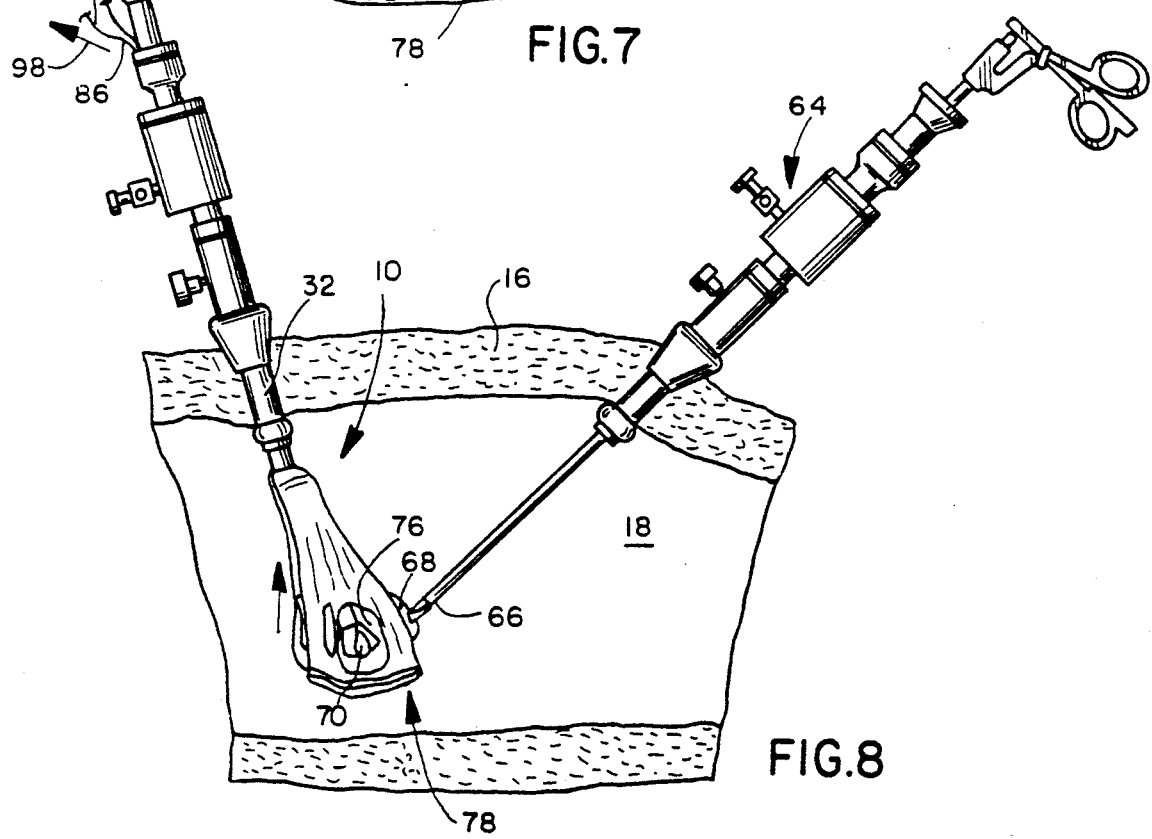

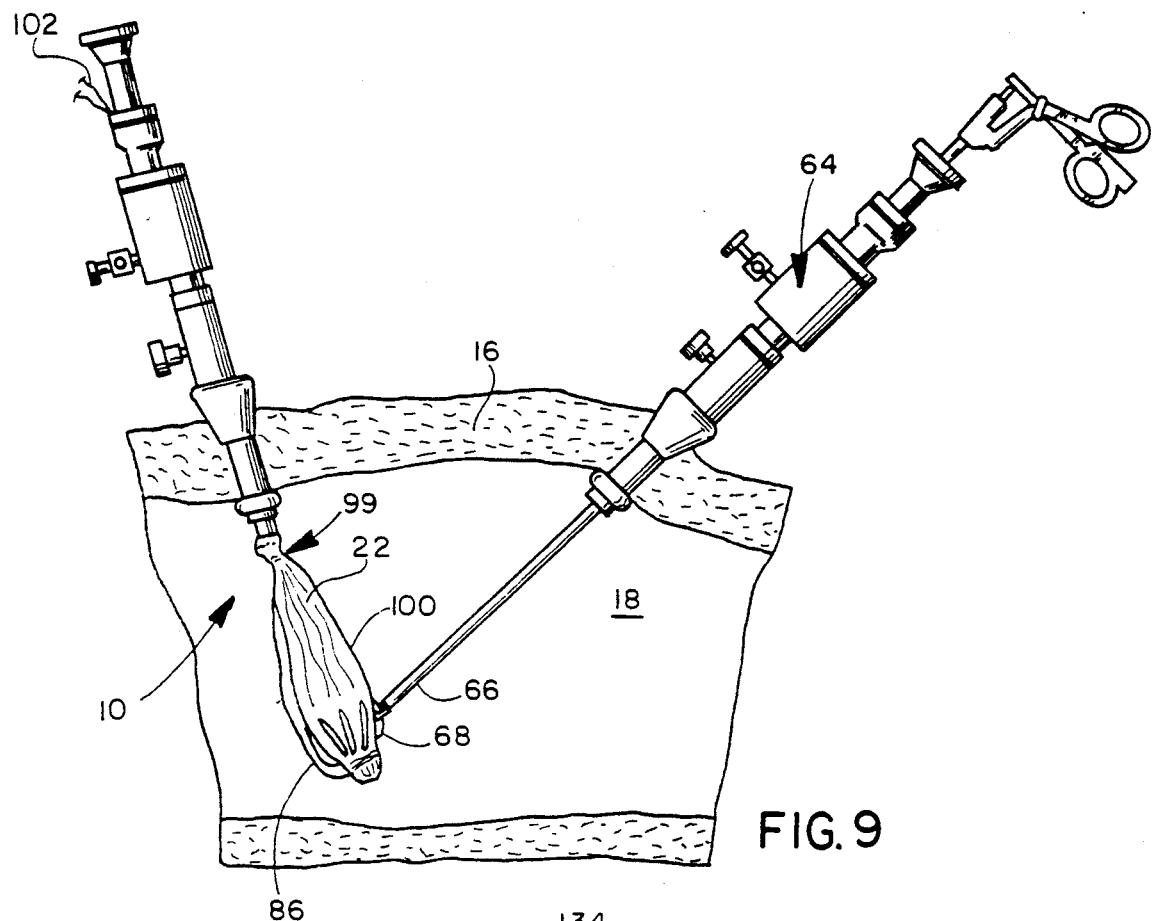
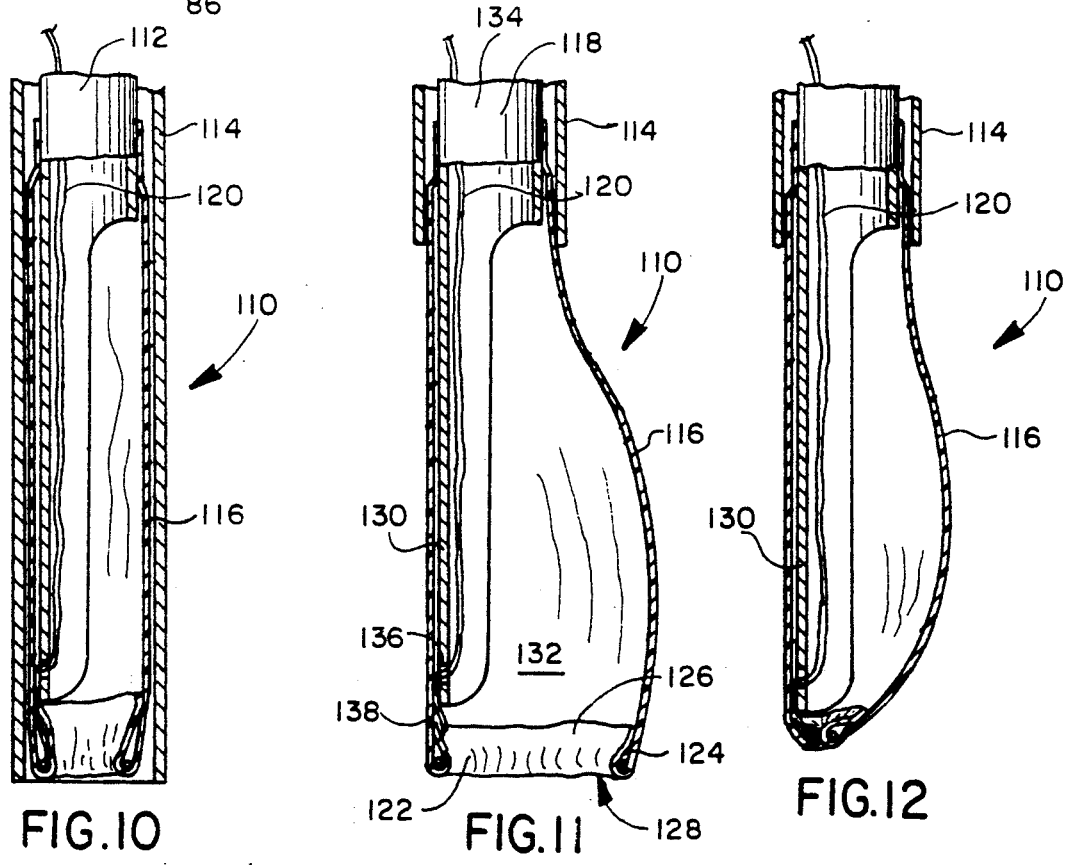
FIG. 9
FIG. 10  FIG. 11  FIG. 12

DISPOSABLE POUCH CONTAINER FOR ISOLATION AND RETRIEVAL OF TISSUES REMOVED AT LAPAROSCOPY

BACKGROUND OF THE INVENTION

1. Field of the Invention

The present invention relates to internal surgery and, more particularly, to an apparatus for safely isolating and removing a mass, growth, or cyst from within an internal body cavity. The invention is also directed to a method of using the apparatus to perform a surgical procedure.

2. Background Art

Advances in laparoscopic instruments and methods, as well as improvements in image resolution obtained by video equipment, have expanded the horizons of operative laparoscopy to new levels of achievement. It is now possible, through laparoscopy, to perform even major surgery on an outpatient basis.

To perform laparoscopic surgery, a sleeve, defining a working passageway, is directed through body tissue into a cavity in which the surgical procedure is to be performed. The cavity is distended by introducing a gas, such as $CO_2$. Several of the sleeves may be employed, depending upon the nature of the procedure. Various types of instruments can be directed through the sleeves to perform the surgery.

One concern with laparoscopic surgery is the fear of disseminating cancerous, infectious, or irritating material from abdominal lesions through spillage from the lesions during removal thereof from within the body cavity. As one example of this problem, when gallbladder surgery is performed, as to remove stones, if no precautions are taken, bile can spread out in the abdomen and cause peritonitis. Similarly, cutting into an infectious lesion may cause exposure of internal organs and tissues to dangerous amounts of noxious puss, or the like, from the lesion.

To avoid these problems, when practicing conventional laparoscopic techniques, surgeons must exercise great care. In so doing, the length of the procedures is often greatly increased, which is obviously undesirable. However, regardless of the care exercised, the abdominal organs may become exposed directly to the harmful contents of a lesion during the operation. Similarly, when a large excised tumor is to be removed from the abdomen, it must be broken down in place and removed, piece by piece, through an abdominal sleeve having a diameter on the order of 10 mm by the process of morcellation. This results in tedious operations which are time consuming and, in spite of caution being exercised, occasionally hazardous. Additionally, fragments of the tumor or tissue which is morcellated may float away from the surgical site and may ultimately be left in the body cavity. This problem is particularly aggravated in operations which require periodic flushing during the performance of the operation. These tumors or tissue fragments may float out of the pelvic cavity during lavage and disappear, at least temporarily, into the abdominal cavity.

SUMMARY OF THE INVENTION

The present invention is specifically directed to overcoming the above enumerated problems in a novel and simple manner.

More particularly, the invention contemplates an apparatus for facilitating the safe removal of a mass from within a body cavity. The apparatus has a membrane that can be selectively placed in a) an expanded state wherein the membrane defines an internal space for reception of a mass to be removed from the cavity and b) a collapsed state wherein the membrane occupies less space than it does in its expanded state. The membrane has an entryway that is in communication with the internal space defined by the membrane with the membrane in its expanded state. Structure is provided for closing the membrane entryway from a location remote from the entryway.

With the inventive structure, a mass in the body cavity can be directed through the membrane entryway into the internal space defined by the membrane and afterwards the entryway can be closed, whereupon escape of the mass in the internal membrane space through the membrane entryway is prevented. Preferably, the membrane is impermeable to the liquid emanating from the mass therewithin to thereby provide a protective barrier around the mass. Once the mass is within the membrane and the entryway is closed, the mass can be decompressed, morcellated, etc. to facilitate its removal without fear of exposure to other organs and tissue.

With the inventive structure, a growth or mass can be excised or removed, whereupon the intact mass/growth, or an entire organ with a mass/growth thereon can be placed safely within the membrane space and the entryway sealed. Once the mass/growth is safely confined, the mass/growth can either be worked upon within the membrane, i.e. decompressed, morcellated, etc., or removed intact with the membrane through an abdominal sleeve or a vaginal opening.

Preferably, an elongate conduit/sleeve is provided and defines an internal passageway. The membrane is connected to the conduit so that the internal conduit passageway is in communication with the internal membrane space with the membrane in its expanded state. This facilitates not only insertion of the membrane into the body cavity but performance of various procedures from externally of the body cavity through the passageway. Desired instruments can be directed through the passageway of the elongate conduit to access the mass to be removed.

Preferably, the membrane has an annular surface that bounds the entryway. The membrane annular surface has a first diameter with the membrane in its expanded state. The closing structure reduces the diameter of the membrane annular surface to a second diameter that is less than the first diameter. In a preferred form, the closing structure has a drawstring to cinch the annular membrane to seal the entryway.

The elongate conduit preferably has a cylindrical wall with a cylindrical surface defining the internal passageway. The cylindrical wall has a forward free end with the internal membrane space defined forwardly of the forward free end of the cylindrical wall. There is preferably an extension forwardly of the forward free end of the cylindrical wall to define a support to facilitate closing of the membrane entryway. With a drawstring being utilized, the extension defines a bearing surface against which the string can be drawn to close the membrane entryway.

In one form of the invention, the membrane surrounds at least a part of the conduit wall. An outer sleeve surrounds the elongate conduit and is movable lengthwise relative thereto between a position wherein the membrane is exposed to be expanded and a position wherein the conduit is partially and preferably entirely within the outer sleeve to thereby facilitate direction of the apparatus through the body tissue bounding the cavity within which the operation is to be performed.

To facilitate the manipulation of the membrane by various instruments in the cavity, at least one tab is provided thereon.

To facilitate pulling of a drawstring, the extension is provided with at least one bore. The bore preferably extends radially with respect to the axis of the conduit. Alternatively, first and second bores are provided in at least one of the extension and conduit. The string extends through one bore to a location wherein it engages the membrane and extends back through the other bore for manipulation from a point remote from the membrane entryway.

In an alternative form of the invention, a pivotable jaw is provided on the conduit. The jaw is movable between open and closed positions and, as it moves from its closed to its open position, draws the membrane into its expanded state.

Cooperating structure is provided on the outer sleeve and elongate conduit to prevent relative rotation therebetween. This allows the surgeon to hold the position of the membrane fixed during the performance of the procedure.

In one form of the invention, the conduit has spaced proximal and distal ends and a cap is provided on the proximal end to selectively seal and expose the proximal end thereof.

To further facilitate performance of certain procedures, structure is provided on the elongate conduit to define two distinct passageways within the single internal passageway defined by the elongate conduit. One passageway can be used for an instrument to hold a growth or cystic mass and the other to facilitate passage of an instrument to drain and/or morcellate the held mass.

In one form of the invention, the membrane defines a sleeve with first and second open ends which can be of the same or different diameter. One of the first and second ends defines the membrane entryway. Structure is provided to close the other of the first and second ends so that a sealed space is defined within the cavity.

The invention also contemplates an apparatus including a membrane that can be placed selectively in expanded and collapsed states and having an entryway in communication with the internal space and an elongate conduit defining an internal passageway with the membrane connected to the elongate conduit so that the internal passageway defined by the elongate conduit is in communication with the internal membrane space. Structure is provided for closing the membrane entryway.

The invention also contemplates a method of removing a severed mass/growth from within a body cavity. The method consists of the steps of placing a collapsible membrane defining an internal space and having an entryway in communication with the internal space in a body cavity containing a severed mass to be removed from the cavity, directing the membrane relative to the mass to be removed from the cavity so that the mass moves through the membrane entryway into the membrane space, and closing the membrane entryway to maintain the mass within the internal membrane space to isolate the mass from the body cavity.

The membrane can be closed by any of a number of different techniques, one of which is accomplished through a drawstring. Preferably the drawstring can be operated from a remote location which allows the membrane to be sealed from a point externally of the cavity.

Preferably, the membrane surrounds an elongate conduit having proximal and distal ends and defining an internal passageway in communication with the internal membrane space. The elongate conduit, according to the invention, is directed into a body cavity so that the proximal end of the elongate conduit is exposed externally of the tissue bounding the body cavity.

A surgical instrument can be directed through the proximal end of the elongate conduit into the membrane internal space to access the growth or mass to be removed from the body cavity.

A suitable instrument can be directed through the elongate conduit to morcellate and/or drain the mass/growth. With the membrane entryway sealed, this can be accomplished without fear of spreading particles from the mass or growth to other organs and tissues in the body cavity.

The invention also contemplates the step of constricting the membrane at a location spaced from the membrane entryway so that the mass is completely sealed in a pouch. The pouch containing the intact mass/growth or decompressed and otherwise diminished organ or growth/mass can then be withdrawn from the abdomen through an abdominal port, or vaginal port in female patients, without fear of contamination of the peritoneal cavity by the contents of the pouch.

BRIEF DESCRIPTION OF THE DRAWINGS

FIGS. 4–9 show the sequence of employing the inventive apparatus to remove a mass from within a body cavity:

FIG. 4 shows the inventive apparatus introduced through a laparoscopy cannula with a stabilizing support structure for holding the position of the apparatus with respect to a tissue such as the abdominal wall;

FIG. 5 shows a second instrument extending through tissue such as the abdominal wall and drawing the membrane towards its expanded state in the vicinity of an excised mass/growth;

FIG. 6 shows the second instrument directing the expanded membrane over the excised mass/growth within the cavity;

FIG. 7 shows an instrument holding the mass/growth from within the membrane in the process of pulling the mass/growth into the internal membrane space;

FIG. 8 shows the membrane entryway being closed;

FIG. 9 shows the membrane being completely sealed to define a self-contained pouch with the mass therein in preparation for withdrawal from the abdomen following decompression of the growth/mass within the membrane by drainage and/or morcellation, as needed.

FIG. 10 is a cross-sectional view of the distal end of a modified form of apparatus according to the present invention with the membrane therein shown in its collapsed state;

FIG. 11 is a view as in FIG. 10 with the membrane shown in its expanded state;

FIG. 12 is a view as in FIGS. 10 and 11 with the membrane entryway closed;

DETAILED DESCRIPTION OF THE DRAWINGS

Figure 1:
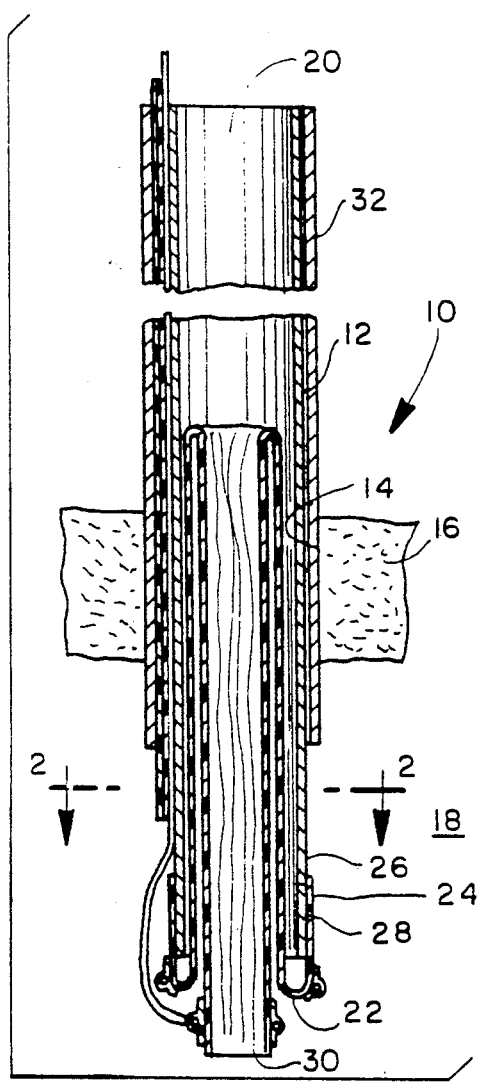
FIG. 1 is a cross sectional view of an apparatus for facilitating safe removal of a mass according to the present invention and including a sleeve/conduit extending through a tissue such as the abdominal wall and having a collapsed protective membrane therewithin.

One form of apparatus for facilitating the safe removal of a growth/mass, or other lesion, from within a body cavity, according to the present invention, is shown at 10 in FIGS. 1-9. The apparatus 10 consists of an elongate, cylindrical conduit/sleeve 12 which is extendable through an incision 14 in a tissue 16 bounding an internal cavity 18, within which a surgical procedure is performed. The conduit/sleeve 12 defines an internal working passageway 20 through which access to the cavity 18 can be gained from a location externally of the body cavity 18.

The conduit/sleeve 12 has a funnel-shaped membrane 22 attached thereto. The smaller diameter end 24 of the membrane closely surrounds the outer surface 26 of the conduit/sleeve 12 at the free end 28 thereof, and is suitably secured thereto, as by an adhesive. The membrane 22 is preferably formed from a durable, yet pliable material, such as MYLAR, polyurethane, or the like.

Figure 3:
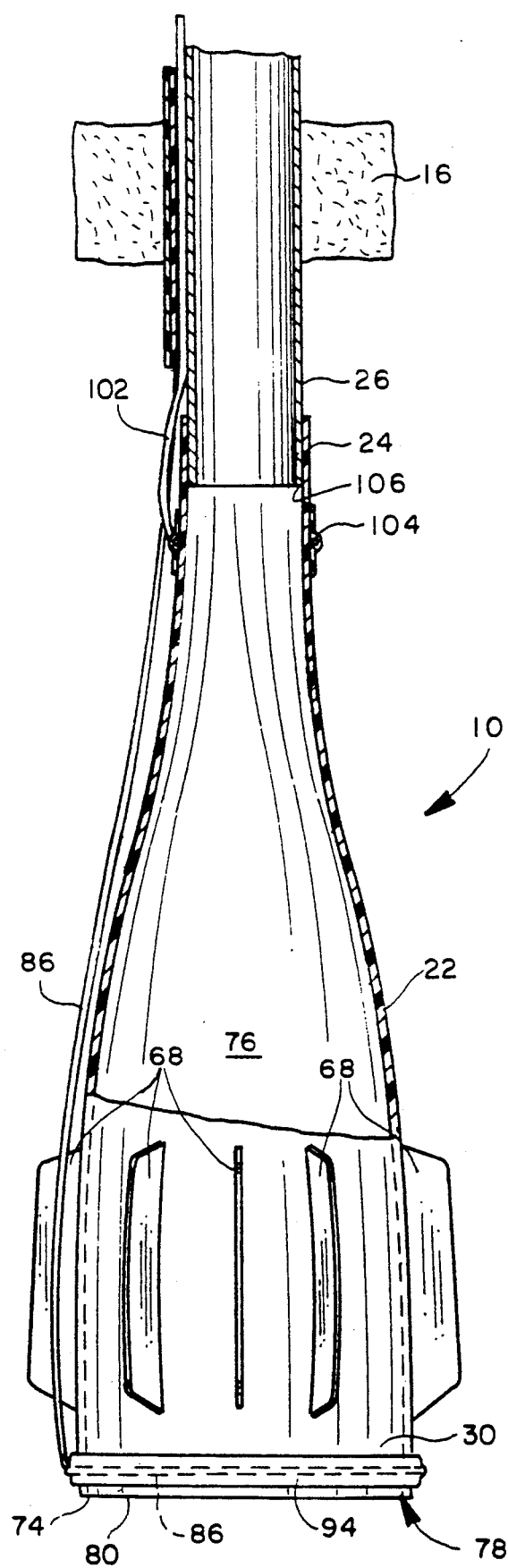
FIG. 3 is a view as in FIG. 1 with the membrane drawn into an expanded state to define an entryway into an internal space bounded by the membrane.

The membrane 22 can be selectively placed in a collapsed state, as shown in FIG. 1, and an expanded state, as shown in FIG. 3. With the membrane 22 in its collapsed state of FIG. 1, substantially the entire membrane 22 is doubled under itself and tucked within the passageway 20 to reside substantially entirely within the diameter of the conduit/sleeve 12. With the membrane 22 folded into the collapsed state of FIG. 1, it can be placed in its expanded state simply by drawing downwardly on the free end 30 of the membrane 22.

FIGS. 4-9 show the preferred sequence of operation utilizing the inventive apparatus 10. An outer sleeve 32, such as a laparoscopy cannula, surrounds the conduit/sleeve 12, penetrates the tissue 16, which is generally the abdominal wall, and serves as a guide for the conduit/sleeve 12. To effect insertion of the sleeve 32, a spike/trocar (not shown) is directed downwardly through the sleeve 32 until its end projects beyond the free, distal end 34 of the sleeve 32. The spike/trocar guides the sleeve 32 into and through the incision 36 in the tissue 16. Once the FIG. 4 position for the sleeve 32 is realized, a membrane 38, situated internally of the cavity 18, is inflated to define a shoulder 40 which abuts the inner wall 42 of the tissue 16 to prevent withdrawal of the sleeve 32.

A collar 44 is slidable lengthwise relative to the sleeve 32. The collar 44 has a cone-shaped end 46 defining a tapered surface 48 which can be pressed against the outer surface 50 of the tissue 16. The tapered surface 48 maintains a leakproof seal around the outer edge of the incision 36. A set screw 52 fixes the collar 44 in its sealed position of FIG. 4.

The membrane 38 and collar 44 cooperatively maintain the sleeve 32 in a relatively rigid, upright state. At the same time, the membrane 38 and collar 44 maintain a leakproof seal around the sleeve 32 to prevent escape of gas from the cavity 18. The cavity 18 is filled with a gas to distend the tissue 16 to enlarge the working space for the surgeon. To accomplish this, gas from a supply 54 is directed through an inlet 56, a one way valve 58 and into the passageway 60 defined internally of the sleeve 32, from where it is communicated with the cavity 18.

Figure 5:
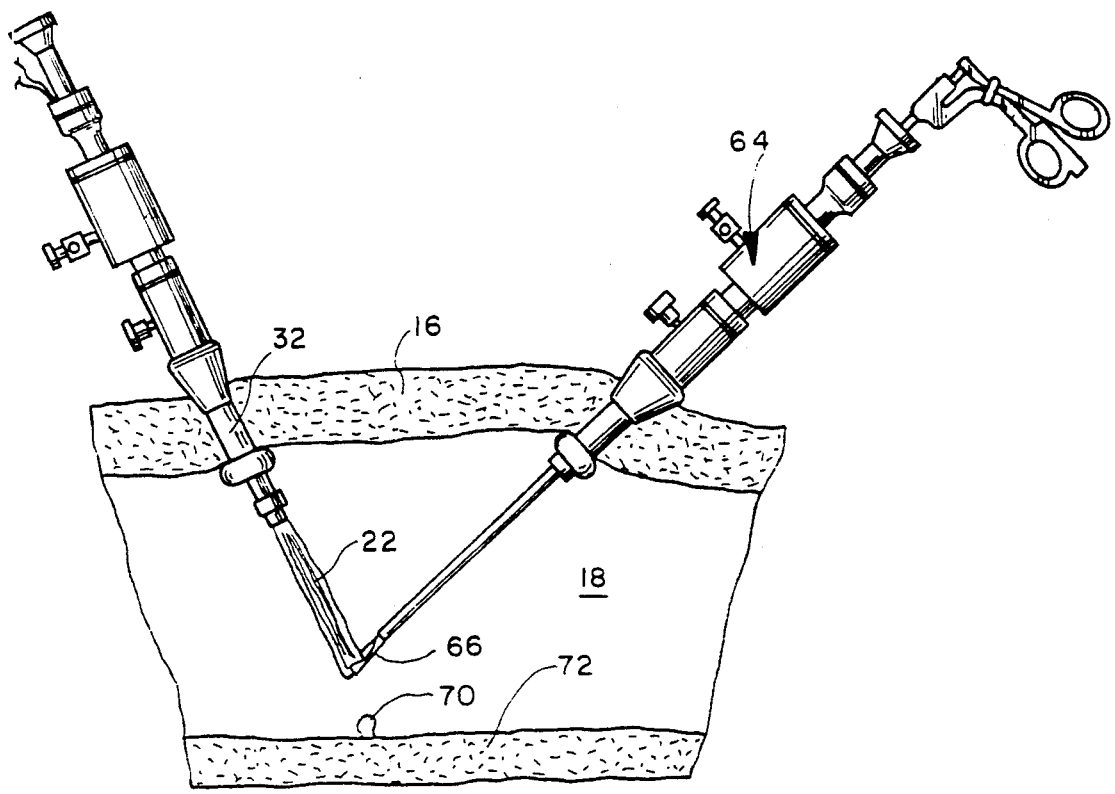

Once the collar 44 is fixed, the conduit/sleeve 12 can be directed downwardly through a gasket 62 and into the outer sleeve 32 for passage therethrough into the cavity 18. Through a second cannula, shown at 64 in FIG. 5 and extending through a spaced incision, the free membrane end 30 is grasped and pulled downwardly out of the conduit/sleeve 12 by means of a forceps 66. A plurality of tabs 68 are provided on the membrane to facilitate manipulation thereof, as by the forceps 66. The membrane 22 is drawn progressively downwardly, as shown in FIG. 5, to the FIG. 6 position, wherein the enlarged free end 30 is directed over a mass/growth 70 which has been removed intact from the organ 72. The bottom annular edge 74 of the membrane 22 is first placed in the vicinity of the mass 70 which is supported on the organ 72, which acts as a platform. The membrane 22, in its expanded state, defines an internal space 76 which is accessible through an entryway 78 bounded by a surface 80 at the free end 30 of the membrane 22.

Figure 6:
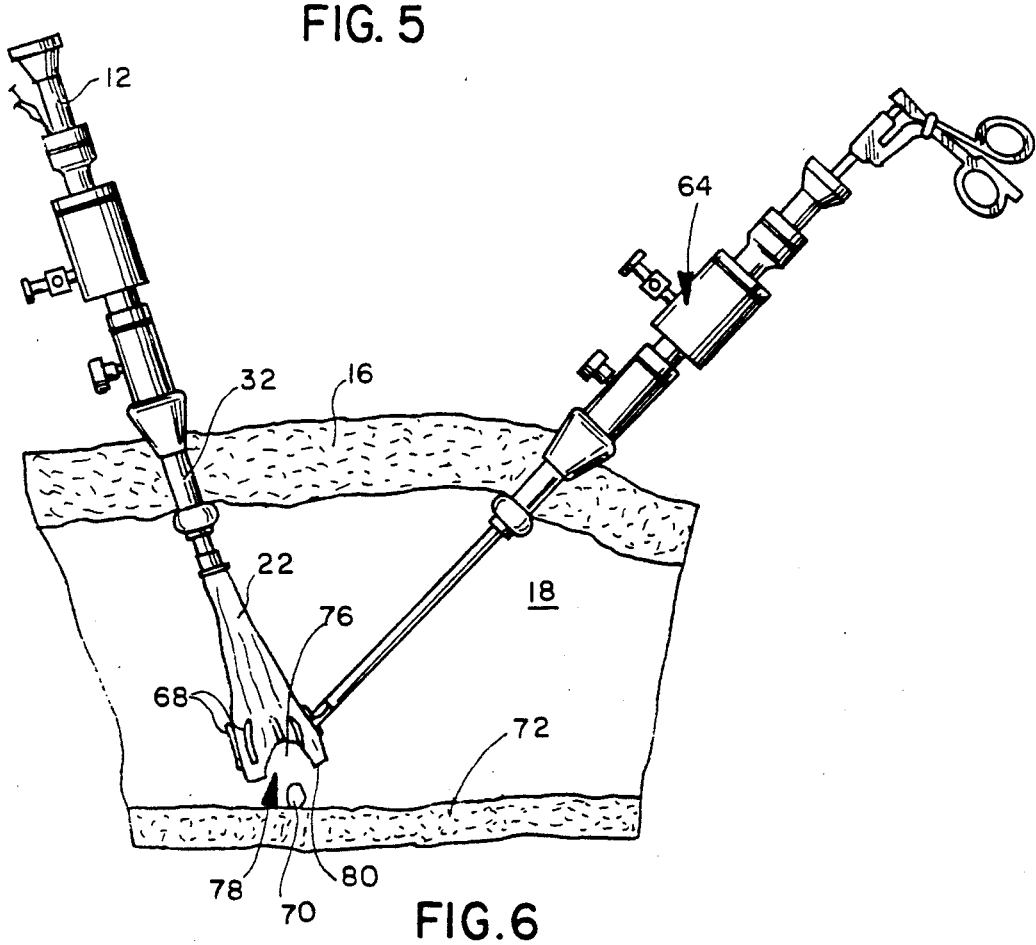
Figure 4:
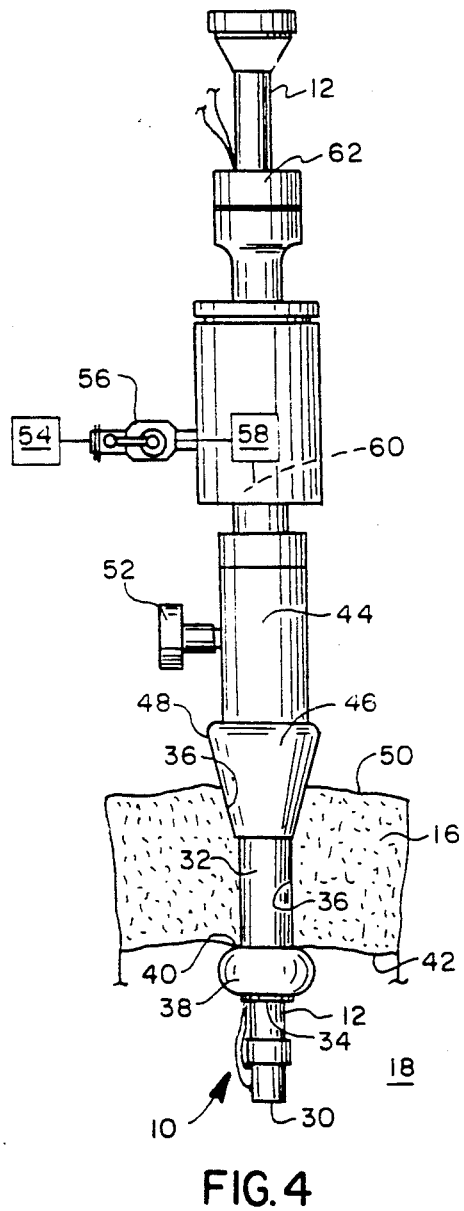

With the membrane 22 positioned as in FIG. 6, an unobstructed communication path is defined through the passageway 20 into the internal space 76 for gaining access to the mass/growth 70. As shown in FIG. 7, an instrument 82, having a grasping end 84, can be directed through the conduit/sleeve 12 and into the space 76 to grasp the mass growth 70 and draw the same through the entryway 78 and into the space 76, after which the entryway 78 is closed.

Figure 2:
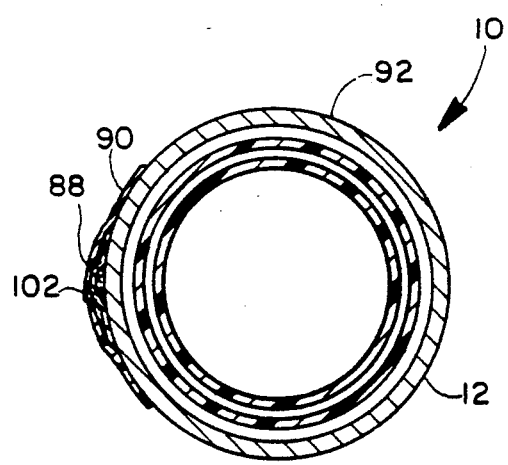
FIG. 2 is a cross-sectional view of the apparatus taken along line 2—2 of FIG. 1.

To effect closing of the entryway 78, a drawstring 86 is provided. The drawstring 86 extends downwardly through a channel 88 defined by a tape 90, or the like, adhered to the outer surface 92 of the conduit/sleeve 12. as seen in FIG. 2 The string 86 extends from a point externally of the tissue 18 i.e. abdominal wall, downwardly through the channel 88 and fully around the free end 30 of the membrane within a surrounding hem 94. The free end of the string 86 can either be attached to the membrane 22 or doubled back through the channel 88.

The forceps 66 inserted through sleeve 64 is used to grasp one of the tabs 68 on the membrane 22 and hold it so that the membrane 22 and particularly the free end 30 thereof in a relatively fixed position. The outer free end 96 of the string 86 can then be drawn upwardly against the held tab 68, as indicated by arrow 98 in FIG. 8, to constrict the membrane free end 30, to thereby close the membrane entryway 78. Once the entryway 78 is closed, as shown in FIG. 9, the membrane 22 provides a barrier to prevent exposure of the mass/growth 70 therewithin to tissue and organs within the body cavity 18.

Access can be gained to the mass/growth 70 through the conduit/sleeve 12. Any desired instrument can be directed through the conduit/sleeve 12 as to morcellate or decompress the mass/growth 70 within the closed space 76. The morcellated mass/growth 70 will be safely confined within the space 76 by the membrane 22 and can be safely isolated and withdrawn.

The invention also contemplates that the mass/growth 70, either intact, decompressed or morcellated, can be withdrawn through the conduit/sleeve 12 in a self-contained pouch. As shown in FIG. 9, the membrane can be closed and severed at 99 to define a self-contained pouch 100 with the mass/growth 70 therewithin, which pouch 100 can be safely removed through either the incision 36 or sleeve or, in the case of a female patient, through the vagina.

A second string 102 extends downwardly through the channel 88 and around the membrane end 24 through a guide sleeve 104. By drawing upwardly on the string 102, the membrane 22 can be cinched at a location above the end 30 and below the bottom edge 106 of the conduit/sleeve 12. By then severing the strings 86, 102, as shown in FIG. 9 the pouch 100 is freely movable within the cavity 18 for safe removal therefrom.

A modified form of the invention is shown in FIGS. 10-12 at 110. The apparatus 110 is usable substantially in the same fashion as the apparatus 10 in FIGS. 1-9. The apparatus 110 consists of an inner conduit 112 with an outer sleeve/housing 114. A funnel-shaped membrane 116 surrounds and is adhered to the bottom free end 118 of the conduit 112. The outer sleeve/housing 114 can be directed downwardly relative to the conduit 112 to radially compress the membrane 116 so that the membrane 116 resides fully within the outer sleeve/housing 114. The membrane 116 can be folded, twisted or otherwise radially compressed to facilitate its placement within the outer sleeve/housing 114 without tearing.

A drawstring 120 extends downwardly through the conduit 112 and around the free end 122 of the membrane 116 within a channel 124 defined by an underturned hem 126.

To facilitate closing of the entryway 128 by the drawstring 120, an extension 130 is provided on the conduit 112 within the internal space 132 bounded by the membrane 116. The extension 130 projects in cantilever fashion from the body 134 of the conduit 112. The extension 130 has a radial bore 136 therethrough to accept the drawstring 120. The drawstring 120 extends downwardly through the conduit 112 and radially outwardly through the bore 136 and into the hem channel 124. The edge 138 of the extension 130 provides a brace against which the string 120 can be borne to cinch the free end 122 of the membrane 116, to thereby close the entryway 128, as shown in FIG. 12 without significant bending of the membrane 116 relative to the conduit 112 or movement of the membrane free end 122 lengthwise relative to the conduit 112.

The string 120 can be cinched in a number of different ways. A conventional hangman's knot, as commonly used to connect fishing tackle to the end of a line, can be employed. Alternatively, a structure can be used as shown in FIGS. 13 and 14.

Figure 13:
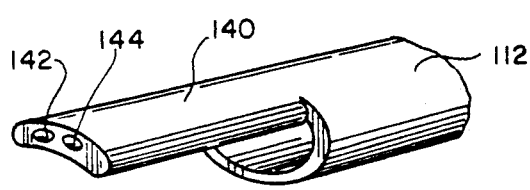
FIG. 13 is an enlarged perspective view of an extension on the inventive apparatus in FIGS. 10-12 for facilitating closing of the membrane entryway through a drawstring.
Figure 14:
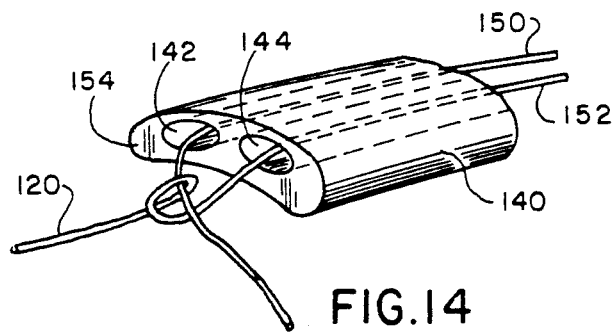
FIG. 14 is an enlarged perspective view of the extension of FIG. 13 with a loosened drawstring thereon.
Figure 15:
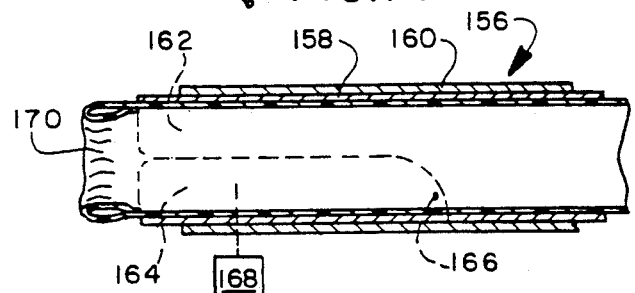
FIG. 15 is a cross-sectional view of a further modified form of apparatus for facilitating safe removal of a mass according to the present invention with a movable jaw thereon and with the membrane on the apparatus shown in its closed/collapsed state.
Figure 16:
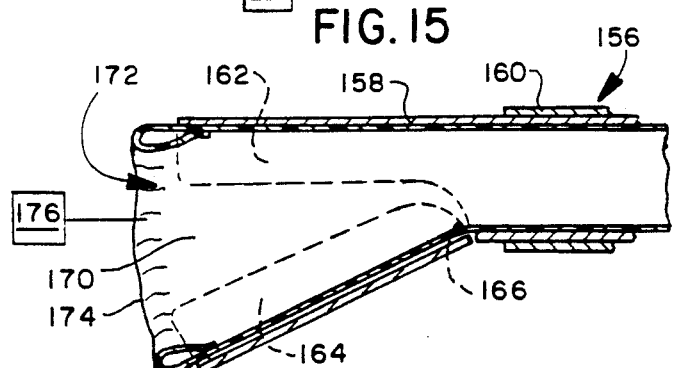
FIG. 16 is a view such as that in FIG. 15 with the membrane in its expanded state.

In FIGS. 13 and 14, the conduit 112 is shown to have an extension 140 with two lengthwise, parallel bores 142, 144. The string 120 can be directed through the bore 142, around the membrane 116, looped around itself and then extended back through the bore 144. Drawing on the string ends 150, 152 causes the line to be cinched at the free end 154 of the extension 140. The string ends 150, 152 can be tied over a curved suture holder or fixed in a V-shaped suture holder mounted on the proximal end of the conduit 112.

A further modified form of the invention is shown in FIGS. 15-18 at 156. The apparatus 156 has an inner conduit 158 and an outer sleeve 160 encompassing the conduit 158. The conduit 158 has an extension 162 with a cooperating jaw 164. The jaw 164 pivots relative to the conduit 158 about a pin 166, or on a plastic hinge (not shown) defined by a slot cut into the conduit 158, between a closed position, shown in FIG. 15, and an open position, shown in FIG. 16. Pivoting of the jaw 164 between its open and closed positions is accomplished by a means 168, which can be a drawstring, or the like. Alternatively, the means 168 could be a spring biasing mechanism for normally biasing the jaw 164 to its open position of FIG. 16. By sliding the outer sleeve 160 from right to left in FIG. 16 relative to the conduit 158, the sleeve 160 progressively cams the jaw 164 into its closed position of FIG. 15. Opposite movement of the sleeve 160 allows the jaw 164 to spring open.

Figure 18:
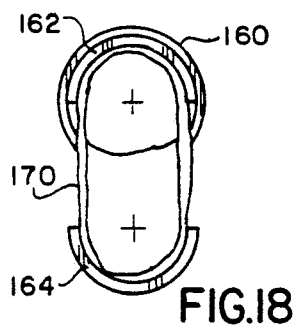
FIG. 18 is a left end view of the apparatus in FIG. 16.
Figure 17:
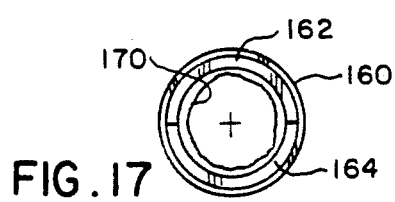
FIG. 17 is a left end view of the apparatus in FIG. 15.

A membrane 170 connects between and is connected to the extension 162 and jaw 164, as by an adhesive, and is collapsible with the jaw 164 in its closed position and movable to an expanded state with the jaw 164 in its open position. As the jaw 164 opens, it draws the membrane 170 with it into a generally oval shape, as shown in FIG. 18.

With the apparatus 156, the outer sleeve 160 is first placed over the jaw 164 after which the apparatus 156 is moved through the tissue 16 into the body cavity to place the entryway 172 for the membrane 170 over a removed/excised mass/growth. The outer sleeve 160 is then backed off to allow the jaw 164 to open fully to allow the membrane 170 to realize its expanded state. The mass/growth is pulled into the membrane 170 by an instrument (not shown) directed through the conduit 158. The free end 174 of the membrane 170 can be cinched, as by a drawstring, or other suitable closing device, shown schematically at 176 in FIG. 16.

Figure 19:
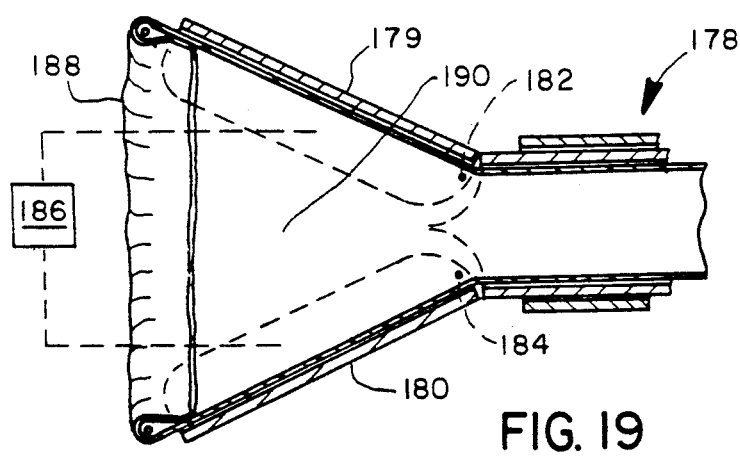
FIG. 19 is a cross-sectional view of a still further modified form of apparatus for facilitating the safe removal of a mass according to the present invention and including two movable jaws.
Figure 20:
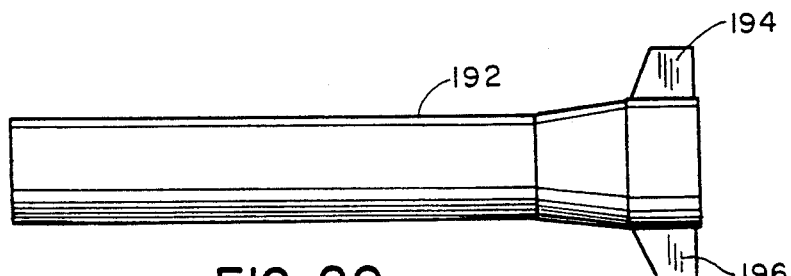
FIG. 20 is a side elevation view of one form of outer sleeve according to the present invention.
Figure 21:
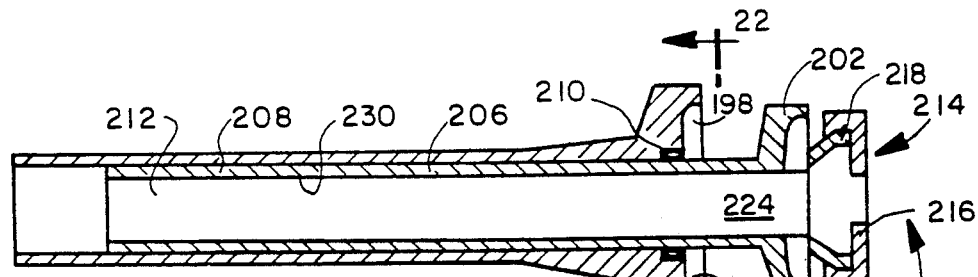
FIG. 21 is a cross-sectional view of a preferred form of inner conduit and outer sleeve placed one within the other in an operative relationship.
Figure 22:
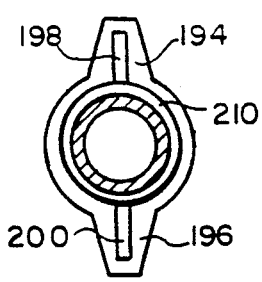
FIG. 22 is a cross-sectional view of the inner conduit and outer sleeve operatively connected and taken along line 22—22 of FIG. 21.
Figure 23:
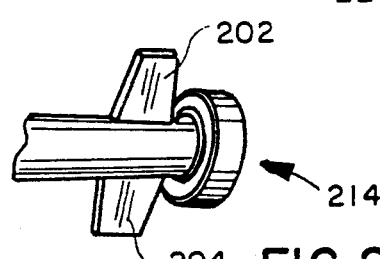
FIG. 23 is a perspective view of the right end of the inner conduit of FIG. 21.

A slightly modified form of apparatus 156 is shown in FIG. 19 at 178. The apparatus has two jaws 179, 180, pivotable respectively about pins 182, 184 between a closed position, shown in solid lines, and an open position, shown in phantom lines. Means, shown schematically at 186, can be used to selectively open and close the jaws 178, 180 and cinch the free end 188 of the membrane 190 connecting between the jaws 178, 180.

A further modification of the present invention is shown in FIGS. 20-23. An outer sleeve 192 has radially oppositely projecting wings 194, 196 defining receptive slots 198, 200 for keying blades 202, 204, projecting radially outwardly from the body 206 of an inner conduit 208. The inner conduit 208 and outer sleeve 192 are used in the same fashion as the corresponding elements in the prior embodiments. The cooperating blades 202, 204 and slots 198, 200 prevent relative rotation between the outer sleeve 192 and inner conduit 208 about the lengthwise axes thereof. A sealing O-ring 210 maintains a leakproof connection between the telescopingly engaged inner conduit 208 and outer sleeve 192.

To prevent escape of gas through the passageway 212 bounded by the inner conduit 208, a cap assembly at 214 is provided. The cap assembly 214 consists of a support 216 mounted on the free end 218 of the inner conduit 108, and a sealing cap 220 hingedly connected to the support 216 for movement between an open position, shown in FIG. 21, and closed position, wherein a plug 222 on the cap 220 seals a receptive bore 224 in the support 216.

Figure 24:
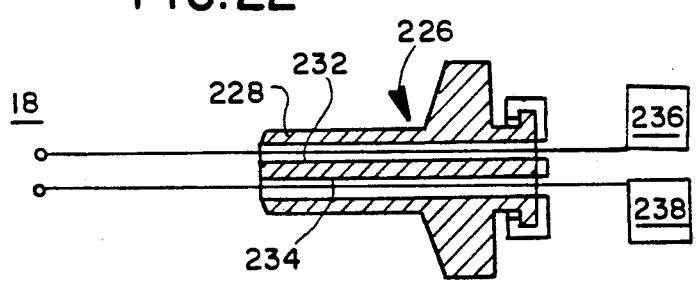
FIG. 24 is a cross sectional view of an insert for the inner conduit that facilitates simultaneous use of a plurality of instruments within the internal membrane space by extension through a single inner conduit.

The invention also contemplates an insert 226, as shown in FIG. 24, for the inner conduit 208. The insert 226 has a resilient, tapered body 228 which is frictionally fit within the inside cylindrical surface 230 of the conduit 208. The insert has parallel, through bores/passageways 232, 234. One of the bores 232 accommodates a holding instrument for the tissue, which instrument is shown schematically at 236. The other bore 234 accommodates a means 238 for diminishing the size of the growth. The means 238 may be either a needle aspiration system or a cutting tool. The holding instrument 236 is used to keep the tissue in a fixed position to allow cutting/decompression thereof without cutting of the membrane within which the operation is being performed.

It can be seen that, with the present invention, cancerous, infected and other types of harmful lesions, excised intact, can be isolated, sealed and safely removed from the abdomen using laparoscopic techniques. A specimen can be submitted to a laboratory in the closed, disposable pouch container 100 without further manipulation. The pouch 100 can also serve as a storage container for a multitude of tissue fragments and/or intact masses removed at different sites within the abdomen. Morcellation of solid masses can be quickly and safely accomplished with the present invention.

The foregoing disclosure of specific embodiments is intended to be illustrative of the broad concepts comprehended by the invention.

We claim:

1. An apparatus for facilitating the safe removal of a mass from within a body cavity, said apparatus comprising:
    a membrane that can be selectively placed in a) an expanded state wherein the membrane defines an internal space for reception of a mass to be removed from a cavity and b) a collapsed state wherein the membrane is compacted from its expanded state;
    an elongate member having a forward free end to which the membrane is attached;
    said membrane having an entryway that is in communication with the internal space defined by the membrane with the membrane in its expanded state; and
    means for closing said membrane entryway from a location remote from said entryway,
    there being a rigid extension on said elongate member separate from said membrane and extending to forwardly of said forward free end of the elongate member to provide a support to facilitate closing of the membrane entryway,
    whereby a mass in a cavity can be directed through the membrane entryway into the internal space defined by the membrane, after which the entryway can be closed, whereupon escape of a mass in the internal membrane space through the membrane entryway is prevented.

2. The apparatus for facilitating the safe removal of a mass from a cavity according to claim 1 wherein said elongate member is an elongate conduit defining an internal passageway and there are means for connecting the membrane to the elongate conduit so that the internal passageway is in communication with the internal membrane space with the membrane in its expanded state.

3. The apparatus for facilitating the safe removal of a mass from a cavity according to claim 1 wherein the membrane has an annular surface that bounds the membrane entryway, said membrane annular surface having a first diameter with the membrane in its expanded state and the means for closing the membrane entryway comprises means for reducing the diameter of the membrane annular surface to a second diameter that is less than the first diameter.

4. The apparatus for facilitating the safe removal of a mass from a cavity according to claim 3 wherein the means for closing the membrane entryway comprises a drawstring to collapse the annular membrane surface that bounds the membrane entryway.

5. The apparatus for facilitating the safe removal of a mass from a cavity according to claim 2 wherein the elongate conduit has a wall with cylindrical surface defining the internal passageway.

6. The apparatus for facilitating the safe removal of a mass from a cavity according to claim 5 wherein the membrane surrounds at least a part of the conduit wall.

7. The apparatus for facilitating the safe removal of a mass from a cavity according to claim 2 wherein the elongate conduit has a cylindrical wall with a cylindrical surface defining the internal passageway, said cylindrical wall having a forward free end, said internal membrane space being defined forwardly of the forward free end of the cylindrical wall, there being an extension forwardly from the forward free end of the cylindrical wall to define a support to facilitate closing of the membrane entryway.

8. The apparatus for facilitating the safe removal of a mass from a cavity according to claim 7 wherein the extension projects in cantilever fashion forwardly from the forward free end of the cylindrical wall.

9. The apparatus for facilitating the safe removal of a mass from a cavity according to claim 6 in combination with an outer sleeve for surrounding the elongate conduit, said outer sleeve and elongate conduit each having a length and being relatively movable in a lengthwise direction between a first relative position wherein the outer sleeve surrounds at least a part of the membrane to prevent the membrane from being placed in its expanded state and a second relative position wherein the membrane can expand fully into its expanded state.

10. The apparatus for facilitating the safe removal of a mass from a cavity according to claim 9 where with the outer sleeve and elongate conduit in their first relative position the membrane resides entirely within the outer sleeve.

11. The apparatus for facilitating the safe removal of a mass from a cavity according to claim 1 wherein the membrane has at least one tab thereon to facilitate manipulation of the membrane within a cavity.

12. An apparatus for facilitating the safe removal of a mass from within a body cavity, said apparatus comprising:
- a membrane that can be selectively placed in a) an expanded state wherein the membrane defines an internal space for reception of a mass to be removed from a cavity and b) a collapsed state wherein the membrane is compacted from its expanded state,
- said membrane having an entryway that is in communication with the internal space defined by the membrane with the membrane in its expanded state;
- means for closing said membrane entryway from a location remote from said entryway,
- whereby a mass in a cavity can be directed through the membrane entryway into the internal space defined by the membrane, after which the entryway can be closed, whereupon escape of a mass in the internal membrane space through the membrane entryway is prevented; and
- an elongate conduit defining an internal passageway and means for connecting the membrane to the elongate conduit so that the internal passageway is in communication with the internal membrane space with the membrane in its expanded state,
- wherein the elongate conduit has a cylindrical wall with a cylindrical surface defining the internal passageway, said cylindrical wall having a forward free end, said internal membrane space being defined forwardly of the forward free end of the cylindrical wall, there being an extension forwardly from the forward free end of the cylindrical wall to define a support to facilitate closing of the membrane entryway,
- wherein the means for closing the membrane entryway includes a string, there being a bore in the extension through which the string extends to facilitate drawing of the string and closing of the membrane entryway from a location remote from the membrane entryway.

13. The apparatus for facilitating the safe removal of a mass from a cavity according to claim 12 wherein at least one of the extension and elongate conduit has first and second bores therethrough, said string extending forwardly through one of the first and second bores into engagement with the membrane and back through the other of the first and second bores.

14. An apparatus for facilitating the same removal of a mass from within a body cavity, said apparatus comprising:
- a membrane that can be selectively placed in a) an expanded state wherein the membrane defines an internal space for reception of a mass to be removed from a cavity and b) a collapsed state wherein the membrane is compacted from its expanded state,
- said membrane having an entryway that is in communication with the internal space defined by the membrane with the membrane in its expanded state;
- means for closing said membrane entryway from a location remote from said entryway,
- whereby a mass in a cavity can be directed through the membrane entryway into the internal space defined by the membrane, after which the entryway can be closed, whereupon escape of a mass in the internal membrane space through the membrane entryway is prevented; and
- an elongate conduit defining an internal passageway and means for connecting the membrane to the elongate conduit so that the internal passageway is in communication with the internal membrane space with the membrane in its expanded state,
- wherein the means for closing the membrane includes at least one jaw that is attached to at least one of the elongate conduit and membrane so as to be pivotable relative to the elongate conduit between open and closed positions, there being cooperating means on the membrane and one jaw for moving the membrane into its expanded state as an incident of the jaw moving from its closed position into its open position.

15. The apparatus for facilitating the safe removal of a mass from a cavity according to claim 9 wherein there are cooperating means on the outer sleeve and elongate conduit for preventing relative rotation between the outer sleeve and elongate conduit with the elongate conduit within the outer sleeve.

16. The apparatus for facilitating the safe removal of a mass from a cavity according to claim 9 wherein the elongate conduit has spaced proximal and distal ends, a cap is provided on the proximal end for selectively sealing and expanding the proximal end of the elongate conduit.

17. The apparatus for facilitating the safe removal of a mass from a cavity according to claim 2 wherein means are provided on the elongate conduit for defining two distinct through passageways within the internal passageway defined by the elongate conduit.

18. The apparatus for facilitating the safe removal of a mass from a cavity according to claim 2 wherein the membrane defines a sleeve with first and second open ends, one of the first and second ends defines the membrane entryway and means are provided for closing the other of the first and second ends so that a mass can be completely sealed within the membrane internal space.

19. An apparatus for facilitating the safe removal of a mass from within a body cavity, said apparatus comprising:
- a membrane that can be selectively placed in a) an expanded state wherein the membrane defines an internal space for reception of a mass to be removed from a cavity and b) a collapsed state wherein the membrane occupies less space than it does in its expanded state,
- said membrane having a free end with an entryway that is in communication with the internal space defined by the membrane with the membrane in its expanded state;
- an elongate conduit defining an internal passageway and having a forward free end;
- means for connecting the membrane to the elongate conduit so that the internal passageway defined by the elongate conduit is in communication with the internal membrane space;
- means for closing the membrane entryway; and
- means adjacent the free end of the membrane on at least one of the membrane and elongate conduit for supporting the free membrane end to facilitate closing of the membrane free end without the membrane free end moving significantly, particularly in a lengthwise direction relative to the elongate conduit, as an incident of the closing means closing the membrane entryway, whereby a mass in a cavity can be directed through the membrane entryway into the internal space defined by the membrane, after which the entryway can be closed, whereupon escape of a mass in the internal membrane space through the membrane entryway is prevented.

20. The apparatus for facilitating the safe removal of a mass from a cavity according to claim 19 wherein the membrane is defined as a sleeve with opposite ends and one sleeve end is attached to the elongate conduit and with the membrane in its collapsed state the membrane is doubled back over the one sleeve end.

21. A method of removing a mass from within a body cavity, said method comprising the steps of:
    placing a collapsible membrane defining an internal space and having an entryway in communication with the internal space inside of a body cavity containing a mass to be removed from the cavity;
    directing the membrane relative to a mass to be removed from the cavity so that the mass moves through the membrane entryway; and
    closing the membrane entryway while supporting the free end of the membrane in a substantially fixed position to maintain the mass within the internal membrane space to prevent exposure of the severed mass within the cavity.

22. The method of removing a mass from within a body cavity according to claim 21 wherein the step of closing the membrane comprises the step of drawing a string around the membrane.

23. The method of removing a mass from within a body cavity according to claim 21 wherein the step of closing the membrane comprises the step of drawing a string around the membrane from a location remote from the membrane entryway.

24. The method of removing a mass from within a body cavity according to claim 21 wherein the membrane surrounds an elongate conduit having proximal and distal ends and defining an internal passageway so that the internal passageway is in communication with the internal membrane space and including the step of directing the elongate conduit into a body cavity so that the proximal end of the elongate conduit is exposed externally of a tissue bounding the body cavity.

25. The method of removing a mass from within a body cavity according to claim 24 including the step of directing a surgical instrument through the proximal end of the elongate conduit and into the membrane internal space to access a growth/mass to be removed from the body cavity.

26. The method of removing a mass from within a body cavity according to claim 25 including the step of cutting up the growth with the surgical instrument to facilitate removal of the mass from the cavity through the elongate conduit.

27. The method of removing a mass from within a body cavity according to claim 21 including the step of constricting the membrane at a location spaced from the membrane entryway so that the mass is completely sealed in the internal membrane space.

28. The method of removing a mass from within a body cavity according to claim 27 including the steps of severing the membrane to define a sealed pouch with mass therein and removing the sealed pouch from the body cavity.

* * * * *